United States Patent
Bikker et al.

(10) Patent No.: US 11,186,619 B2
(45) Date of Patent: *Nov. 30, 2021

(54) ANTIMICROBIAL PEPTIDES BASED ON CMAP27

(71) Applicant: Universiteit Utrecht Holding B.V., Utrecht (NL)

(72) Inventors: Floris Jacob Bikker, Gouda (NL); Albert van Dijk, Zeist (NL); Rosalia Mars-Groenendijk, Nootdorp (NL); Edwin Johannes Adrianus Veldhuizen, Utrecht (NL); Desiree van der Kleij, Zoetermeer (NL); Hendrik Haagsman, Zeist (NL); Elisabeth Margaretha Molhoek, Rotterdam (NL)

(73) Assignee: Universiteit Utrecht Holding B.V., Utrecht (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/380,790

(22) Filed: Apr. 10, 2019

(65) Prior Publication Data

US 2019/0233483 A1     Aug. 1, 2019

Related U.S. Application Data

(60) Division of application No. 14/669,228, filed on Mar. 26, 2015, now Pat. No. 10,301,363, which is a continuation of application No. 13/201,070, filed as application No. PCT/NL2010/050068 on Feb. 12, 2010, now Pat. No. 9,006,174.

(30) Foreign Application Priority Data

Feb. 13, 2009 (EP) .................... 09152810

(51) Int. Cl.
| | |
|---|---|
| C07K 14/465 | (2006.01) |
| A61K 38/17 | (2006.01) |
| A61P 31/04 | (2006.01) |
| A61K 39/39 | (2006.01) |
| C07K 7/08 | (2006.01) |
| C07K 14/47 | (2006.01) |
| A61K 39/00 | (2006.01) |

(52) U.S. Cl.
CPC ............ *C07K 14/465* (2013.01); *A61K 39/39* (2013.01); *C07K 7/08* (2013.01); *C07K 14/47* (2013.01); *A61K 2039/55516* (2013.01)

(58) Field of Classification Search
None
See application file for complete search history.

(56) References Cited

FOREIGN PATENT DOCUMENTS

WO   WO 2007/064903   6/2007

OTHER PUBLICATIONS

International Preliminary Report on Patentability issued in PCT/NL2010/050068 dated Aug. 16, 2011 (8 pages).
International Search Report and Written Opinion issued in PCT/NL2010/050068 dated Jun. 30, 2010 (12 pages).
UniProtKB/TrEMBL Accession No. Q2IAL7 (accessed May 16, 2014 at URL uniprot.org/uniprot/Q2IAL7).
Van Dijk et al., "Chicken heterophils are recruited to the site of *Salmonella* infection and release antibacterial mature Cathelicidin-2 upon stimulation with LPS," Molecular Immunology, 46(7):1517-1526 (2009).
Van Dijk et al., "CMAP27, a novel chicken cathelicidin-like antimicrobial protein," Veterinary Immunology and Immunopathology, 106:321-327 (2005).
Van Dijk et al., "Identification of chicken cathelicidin-2 core elements involved in antibacterial and immunomodulatoiy activities," Molecular Immunology, 46(13):2465-2473 (2009).
Xiao et al., "Identification and functional characterization of three chicken cathelicidins with potent antimicrobial activity," J. Biol. Chem., 281:2858-2867 (2006).

*Primary Examiner* — Julie Ha
*Assistant Examiner* — Kristina M Hellman
(74) *Attorney, Agent, or Firm* — Fish & Richardson P.C.

(57) ABSTRACT

The invention concerns derivatives of CMAP27, which have a good antimicrobial activity and a low haemolytic activity as compared to the wild-type CMAP27 peptide. These derivatives can be used for antibiotic therapy or in a bacteriocidal composition. Further comprised in the invention is the use of CMAP27 and/or its derivatives as adjuvant.

10 Claims, No Drawings
Specification includes a Sequence Listing.

SEQUENCE LISTING

```
<160> NUMBER OF SEQ ID NOS: 28

<210> SEQ ID NO 1
<211> LENGTH: 27
<212> TYPE: PRT
<213> ORGANISM: Gallus gallus

<400> SEQUENCE: 1

Arg Phe Gly Arg Phe Leu Arg Lys Ile Arg Arg Phe Arg Pro Lys Val
1               5                   10                  15

Thr Ile Thr Ile Gln Gly Ser Ala Arg Phe Gly
            20                  25

<210> SEQ ID NO 2
<211> LENGTH: 13
<212> TYPE: PRT
<213> ORGANISM: Artificial
<220> FEATURE:
<223> OTHER INFORMATION: consensus 1 CMAP27 derivative
<220> FEATURE:
<221> NAME/KEY: VARIANT
<222> LOCATION: (2)..(2)
<223> OTHER INFORMATION: L , Y or W
<220> FEATURE:
<221> NAME/KEY: VARIANT
<222> LOCATION: (5)..(5)
<223> OTHER INFORMATION: L, Y or W
<220> FEATURE:
<221> NAME/KEY: VARIANT
<222> LOCATION: (12)..(12)
<223> OTHER INFORMATION: L, Y or W
<220> FEATURE:
```

```
<221> NAME/KEY: VARIANT
<222> LOCATION: (13)..(13)
<223> OTHER INFORMATION: Xaa can be 0-9 of any amino acid

<400> SEQUENCE: 2

Arg Phe Gly Arg Phe Leu Arg Lys Ile Arg Arg Phe Xaa
1               5                   10

<210> SEQ ID NO 3
<211> LENGTH: 13
<212> TYPE: PRT
<213> ORGANISM: Artificial
<220> FEATURE:
<223> OTHER INFORMATION: consensus 2 CMAP27 derivative
<220> FEATURE:
<221> NAME/KEY: VARIANT
<222> LOCATION: (2)..(2)
<223> OTHER INFORMATION: L, Y or W
<220> FEATURE:
<221> NAME/KEY: VARIANT
<222> LOCATION: (5)..(5)
<223> OTHER INFORMATION: L, Y or W
<220> FEATURE:
<221> NAME/KEY: VARIANT
<222> LOCATION: (12)..(12)
<223> OTHER INFORMATION: L, Y or W

<400> SEQUENCE: 3

Arg Phe Gly Arg Phe Leu Arg Lys Ile Arg Arg Phe Arg
1               5                   10

<210> SEQ ID NO 4
<211> LENGTH: 15
<212> TYPE: PRT
<213> ORGANISM: Artificial
<220> FEATURE:
<223> OTHER INFORMATION: consensus 3 CMAP27 derivative
<220> FEATURE:
<221> NAME/KEY: VARIANT
<222> LOCATION: (2)..(2)
<223> OTHER INFORMATION: L, Yor W
<220> FEATURE:
<221> NAME/KEY: VARIANT
<222> LOCATION: (5)..(5)
<223> OTHER INFORMATION: L, Y or W
<220> FEATURE:
<221> NAME/KEY: VARIANT
<222> LOCATION: (12)..(12)
<223> OTHER INFORMATION: L, Y or W
<220> FEATURE:
<221> NAME/KEY: VARIANT
<222> LOCATION: (14)..(14)
<223> OTHER INFORMATION: G or L

<400> SEQUENCE: 4

Arg Phe Gly Arg Phe Leu Arg Lys Ile Arg Arg Phe Arg Pro Lys
1               5                   10                  15

<210> SEQ ID NO 5
<211> LENGTH: 21
<212> TYPE: PRT
<213> ORGANISM: Artificial
<220> FEATURE:
<223> OTHER INFORMATION: CMAP27 derivative

<400> SEQUENCE: 5

Arg Phe Gly Arg Phe Leu Arg Lys Ile Arg Arg Phe Arg Pro Lys Val
1               5                   10                  15

Thr Ile Thr Ile Gln
            20
```

-continued

```
<210> SEQ ID NO 6
<211> LENGTH: 21
<212> TYPE: PRT
<213> ORGANISM: Artificial
<220> FEATURE:
<223> OTHER INFORMATION: consensus 3 CMAP27 derivative
<220> FEATURE:
<221> NAME/KEY: VARIANT
<222> LOCATION: (2)..(2)
<223> OTHER INFORMATION: L, Y or W
<220> FEATURE:
<221> NAME/KEY: VARIANT
<222> LOCATION: (5)..(5)
<223> OTHER INFORMATION: L, Y or W
<220> FEATURE:
<221> NAME/KEY: VARIANT
<222> LOCATION: (12)..(12)
<223> OTHER INFORMATION: L, Y or W
<220> FEATURE:
<221> NAME/KEY: VARIANT
<222> LOCATION: (14)..(14)
<223> OTHER INFORMATION: G or L

<400> SEQUENCE: 6

Arg Phe Gly Arg Phe Leu Arg Lys Ile Arg Arg Phe Arg Pro Lys Val
1               5                   10                  15

Thr Ile Thr Ile Gln
            20

<210> SEQ ID NO 7
<211> LENGTH: 15
<212> TYPE: PRT
<213> ORGANISM: Artificial
<220> FEATURE:
<223> OTHER INFORMATION: CMAP15

<400> SEQUENCE: 7

Arg Phe Gly Arg Phe Leu Arg Lys Ile Arg Arg Phe Arg Pro Lys
1               5                   10                  15

<210> SEQ ID NO 8
<211> LENGTH: 26
<212> TYPE: PRT
<213> ORGANISM: Artificial
<220> FEATURE:
<223> OTHER INFORMATION: consensus 3 CMAP27 derivative
<220> FEATURE:
<221> NAME/KEY: MOD_RES
<222> LOCATION: (26)..(26)
<223> OTHER INFORMATION: AMIDATION

<400> SEQUENCE: 8

Arg Phe Gly Arg Phe Leu Arg Lys Ile Arg Arg Phe Arg Pro Lys Val
1               5                   10                  15

Thr Ile Thr Ile Gln Gly Ser Ala Arg Phe
            20                  25

<210> SEQ ID NO 9
<211> LENGTH: 26
<212> TYPE: PRT
<213> ORGANISM: Artificial
<220> FEATURE:
<223> OTHER INFORMATION: CMAP26

<400> SEQUENCE: 9

Arg Phe Gly Arg Phe Leu Arg Lys Ile Arg Arg Phe Arg Pro Lys Val
1               5                   10                  15

Thr Ile Thr Ile Gln Gly Ser Ala Arg Phe
```

```
            20                  25

<210> SEQ ID NO 10
<211> LENGTH: 26
<212> TYPE: PRT
<213> ORGANISM: Artificial
<220> FEATURE:
<223> OTHER INFORMATION: CMAP26 P14G

<400> SEQUENCE: 10

Arg Phe Gly Arg Phe Leu Arg Lys Ile Arg Arg Phe Arg Gly Lys Val
1               5                   10                  15

Thr Ile Thr Ile Gln Gly Ser Ala Arg Phe
            20                  25

<210> SEQ ID NO 11
<211> LENGTH: 26
<212> TYPE: PRT
<213> ORGANISM: Artificial
<220> FEATURE:
<223> OTHER INFORMATION: CMAP26 P14L

<400> SEQUENCE: 11

Arg Phe Gly Arg Phe Leu Arg Lys Ile Arg Arg Phe Arg Leu Lys Val
1               5                   10                  15

Thr Ile Thr Ile Gln Gly Ser Ala Arg Phe
            20                  25

<210> SEQ ID NO 12
<211> LENGTH: 21
<212> TYPE: PRT
<213> ORGANISM: Artificial
<220> FEATURE:
<223> OTHER INFORMATION: CMAP21

<400> SEQUENCE: 12

Arg Phe Gly Arg Phe Leu Arg Lys Ile Arg Arg Phe Arg Pro Lys Val
1               5                   10                  15

Thr Ile Thr Ile Gln
            20

<210> SEQ ID NO 13
<211> LENGTH: 15
<212> TYPE: PRT
<213> ORGANISM: Artificial
<220> FEATURE:
<223> OTHER INFORMATION: CMAP15 F2L

<400> SEQUENCE: 13

Arg Leu Gly Arg Phe Leu Arg Lys Ile Arg Arg Phe Arg Pro Lys
1               5                   10                  15

<210> SEQ ID NO 14
<211> LENGTH: 15
<212> TYPE: PRT
<213> ORGANISM: Artificial
<220> FEATURE:
<223> OTHER INFORMATION: CMAP15 F5L

<400> SEQUENCE: 14

Arg Phe Gly Arg Leu Leu Arg Lys Ile Arg Arg Phe Arg Pro Lys
1               5                   10                  15

<210> SEQ ID NO 15
<211> LENGTH: 15
```

```
<212> TYPE: PRT
<213> ORGANISM: Artificial
<220> FEATURE:
<223> OTHER INFORMATION: CMAP15 F12L

<400> SEQUENCE: 15

Arg Phe Gly Arg Phe Leu Arg Lys Ile Arg Arg Leu Arg Pro Lys
1               5                   10                  15

<210> SEQ ID NO 16
<211> LENGTH: 15
<212> TYPE: PRT
<213> ORGANISM: Artificial
<220> FEATURE:
<223> OTHER INFORMATION: CMAP15 3xF-L

<400> SEQUENCE: 16

Arg Leu Gly Arg Leu Leu Arg Lys Ile Arg Arg Leu Arg Pro Lys
1               5                   10                  15

<210> SEQ ID NO 17
<211> LENGTH: 15
<212> TYPE: PRT
<213> ORGANISM: Artificial
<220> FEATURE:
<223> OTHER INFORMATION: CMAP15 F2W

<400> SEQUENCE: 17

Arg Trp Gly Arg Phe Leu Arg Lys Ile Arg Arg Phe Arg Pro Lys
1               5                   10                  15

<210> SEQ ID NO 18
<211> LENGTH: 15
<212> TYPE: PRT
<213> ORGANISM: Artificial
<220> FEATURE:
<223> OTHER INFORMATION: CMAP15 F5W

<400> SEQUENCE: 18

Arg Phe Gly Arg Trp Leu Arg Lys Ile Arg Arg Phe Arg Pro Lys
1               5                   10                  15

<210> SEQ ID NO 19
<211> LENGTH: 15
<212> TYPE: PRT
<213> ORGANISM: Artificial
<220> FEATURE:
<223> OTHER INFORMATION: CMAP15 F12W

<400> SEQUENCE: 19

Arg Phe Gly Arg Phe Leu Arg Lys Ile Arg Arg Trp Arg Pro Lys
1               5                   10                  15

<210> SEQ ID NO 20
<211> LENGTH: 15
<212> TYPE: PRT
<213> ORGANISM: Artificial
<220> FEATURE:
<223> OTHER INFORMATION: CMAP15 3xF-W

<400> SEQUENCE: 20

Arg Trp Gly Arg Trp Leu Arg Lys Ile Arg Arg Trp Arg Pro Lys
1               5                   10                  15

<210> SEQ ID NO 21
<211> LENGTH: 13
<212> TYPE: PRT
```

<213> ORGANISM: Artificial
<220> FEATURE:
<223> OTHER INFORMATION: CMAP13

<400> SEQUENCE: 21

Arg Phe Gly Arg Phe Leu Arg Lys Ile Arg Arg Phe Arg
1               5                   10

<210> SEQ ID NO 22
<211> LENGTH: 12
<212> TYPE: PRT
<213> ORGANISM: Artificial
<220> FEATURE:
<223> OTHER INFORMATION: CMAP12

<400> SEQUENCE: 22

Arg Phe Gly Arg Phe Leu Arg Lys Ile Arg Arg Phe
1               5                   10

<210> SEQ ID NO 23
<211> LENGTH: 11
<212> TYPE: PRT
<213> ORGANISM: Artificial
<220> FEATURE:
<223> OTHER INFORMATION: CMAP11

<400> SEQUENCE: 23

Arg Phe Gly Arg Phe Leu Arg Lys Ile Arg Arg
1               5                   10

<210> SEQ ID NO 24
<211> LENGTH: 10
<212> TYPE: PRT
<213> ORGANISM: Artificial
<220> FEATURE:
<223> OTHER INFORMATION: CMAP10

<400> SEQUENCE: 24

Arg Phe Gly Arg Phe Leu Arg Lys Ile Arg
1               5                   10

<210> SEQ ID NO 25
<211> LENGTH: 14
<212> TYPE: PRT
<213> ORGANISM: Artificial
<220> FEATURE:
<223> OTHER INFORMATION: CMAP2-15

<400> SEQUENCE: 25

Phe Gly Arg Phe Leu Arg Lys Ile Arg Arg Phe Arg Pro Lys
1               5                   10

<210> SEQ ID NO 26
<211> LENGTH: 13
<212> TYPE: PRT
<213> ORGANISM: Artificial
<220> FEATURE:
<223> OTHER INFORMATION: CMAP3-15

<400> SEQUENCE: 26

Gly Arg Phe Leu Arg Lys Ile Arg Arg Phe Arg Pro Lys
1               5                   10

<210> SEQ ID NO 27
<211> LENGTH: 12
<212> TYPE: PRT
<213> ORGANISM: Artificial

```
<220> FEATURE:
<223> OTHER INFORMATION: CMAP4-15

<400> SEQUENCE: 27

Arg Phe Leu Arg Lys Ile Arg Arg Phe Arg Pro Lys
1               5                   10

<210> SEQ ID NO 28
<211> LENGTH: 11
<212> TYPE: PRT
<213> ORGANISM: Artificial
<220> FEATURE:
<223> OTHER INFORMATION: CMAP5-15

<400> SEQUENCE: 28

Phe Leu Arg Lys Ile Arg Arg Phe Arg Pro Lys
1               5                   10
```

ANTIMICROBIAL PEPTIDES BASED ON CMAP27

This application is a divisional application of U.S. patent application Ser. No. 14/669,228, filed Mar. 26, 2015 (issued as U.S. Pat. No. 10,301,363), which is a continuation application of U.S. patent application Ser. No. 13/201,070, filed Aug. 11, 2011 (issued as U.S. Pat. No. 9,006,174), which is a U.S. National Phase Patent Application under 35 U.S.C. § 371 of International Application Patent No. PCT/NL2010/050068, filed on Feb. 12, 2010, which claims the benefit of European Patent Application No. 09152810.9, filed on Feb. 13, 2009, the entire contents of which are hereby incorporated by reference in their entireties.

The invention relates to the field of antibiotics, more specifically to peptide antibiotics, especially CMAP27 derivatives.

INTRODUCTION

The ever increasing number of multi-drug resistant pathogens has urged the need for new antibiotics. In the last decade scientists have put much effort in the developments of novel antibacterial agents as well as improvement of current chemotherapeutic agents. Interestingly, many mammals and insects are remarkably resistant to bacterial infection, due to their ability to produce small-sized cationic peptides. This form of protection, an important part of the innate immune system, provides a first line of defence against invading pathogens. Many scientists have focused their attention on these antimicrobial peptides (AMP) as they are currently regarded as an important pool of potentially novel antibiotics.

Thus far, many types of antimicrobial peptides have been isolated and sequences from various sources during past decades (for selected reviews, see: Otvos Jr., L. *Cell. Mol. Life Sci.* 2002, 59:1138; Otvos, Jr., L. *J. Peptide Sci.* 2000, 6:497; Tan, Y.-T. et al., *Mol. Med. Today* 2000, 6:309; Scott, M. G. and Hancock, R. E. W., *Crit. Rev. Immunol.* 2000, 20:407; Hancock, R. E. W. and Chapple, D. S. *Antimicrob. Agents Chemother.* 1999, 43:1317; Hetru, C. et al., In: *Molecular Mechanisms of Immune Responses in Insects*; Brey, P. and Hultmark, D. Ed., Chapman and Hall, London, 1998, pp. 40-66; Hancock, R. E. W. et al., *Adv. Microb. Physiol.* 1995 37:135; Vaara, M. *Microbiol. Rev.* 1992, 395). Within mammals and birds most antimicrobial peptides discovered up to date belong to the cathelicidin and defensin superfamily. Cathelicidins have been found to be widely distributed among divergent species, i.e. in mammals, birds, fish and reptiles, indicating their evolutionary importance, but their repertoire differs considerably among species. Antimicrobial peptides of the cathelicidin family are encoded in the genome as prepropeptides and are proteolytically cleaved to form biologically active peptides ranging from 12 to 97 amino acids (Ramanathan, B. et al., 2002, Microbes Infect. 4:361-372). Based on their typical primary and secondary structure, the released C-terminal peptides can be divided into four main classes, namely 1) α-helical peptides, linear peptides that adopt an amphipathic structure when in contact with environments mimicking biological membranes (LL-37, Agerberth, B., et al., *PNAS* 1995, 92:195; SMAP-29, Anderson, R. C., et al., *Antimicrob. Agents Chemother.* 2004, 48:673); β-hairpin peptides, short cyclic peptides formed by one or two intramolecular disulfide bridges (protegrins, Kokryakov, V. N., et al., FEBS Lett. 1993, 327:231; dodecapeptide, Romeo, D., et al., *J. Biol. Chem.* 1988, 263:9573); 3) tryptophan-rich peptides (indolicidin) (Indolicidin, Selsted, M. E., et al., *J. Biol. Chem.* 1992, 267:4292) and 4) proline/arginine-rich peptides (bactenecins, Gennaro, R., et al., *Infect. Immun.* 1989, 57:3142; PR39, Agerberth, B., et al., *Eur. J. Biochem.* 1991, 202:849).

Most cathelicidins show broad activity against several Gram-negative and Gram-positive bacteria, fungi, protozoa and enveloped viruses (Zaiou, M. and Gallo, R. L., 2002, J. Mol. Med. 80:549-561). Van Dijk et al., (2005, Vet. Immunol. Immunopath. 106:321-327) found a new protein of the cathelicidin family in chicken. It belongs to the group 1 (a-helical) peptides and has been denominated CMAP27, but is also known as CATH-2. Like other members of the cathelicidin family CMAP27 is encoded as a prepropeptide (154 amino acids) and after proteolytic processing, a 27 amino acid long C-terminal peptide is released that has demonstrated potent broad spectrum antimicrobial activity. The amino acid sequence of this C-terminal peptide, called CMAP27, is RFGRFLRKIRRFRPKVTITIQGSARFG (SEQ ID NO: 1).

SUMMARY OF THE INVENTION

Surprisingly it has now been found that C-terminally truncated derivates from CMAP27 and variants thereof yield antimicrobial peptides with equal or more potent antimicrobial and/or immunomodulatory activity and which, importantly, do not affect human blood cells.

Thus the invention is directed to novel CMAP27 derivatives having the general amino acid sequence $RX_1GRX_2LRKIRRX_3X_4$ (SEQ ID NO: 2), in which $X_1$, $X_2$ and $X_3$ can independently be F, L, W, or Y, and $X_4$ can be 0-9 amino acids, preferably the amino acid sequence R (SEQ ID NO: 3), $RX_5K$ (SEQ ID NO: 4), $RX_5KVT$ (SEQ ID NO: 5) or $RX_5KVTITIQ$ (SEQ ID NO: 6), wherein $X_5$ is P, G or L, preferably P.

Also part of the invention are methods to produce the above-mentioned novel antibiotic compounds.

Further part of the invention are pharmaceutical compositions comprising one or more of the peptides of the invention, whether or not in the presence of other pharmaceutically active compounds.

Also part of the invention is the use of a peptide according to the invention as a pharmaceutical and/or for the preparation of a medicament that can be used as an antibiotic.

In another embodiment the invention comprises the use of CMAP27 and the CMAP27 derivatives as described above as for boosting the immune response. Preferably said use is accomplished by using them as adjuvants in vaccine preparations.

DETAILED DESCRIPTION OF THE INVENTION

"CMAP27" as used herein is defined as the protein having the amino acid sequence RFGRFLRKIRRFRPKVTITIQGSARFG (SEQ ID NO: 1), but also the C-terminally amidated version RFGRFLRKIRRFRPKVTITIQGSARF-NH$_2$ (SEQ ID NO: 8), also denominated as CMAP1-26-NH2, is comprised in this definition. It is suggested that CMAP1-26-NH2 is the active form of the peptide, since it is known in cathelicidins that amidation of the C-terminal glycine residue adds to the functionality (Shinnar, A. E. et al., 2003, Bioorg. Chem. 31:425-436; Tomasinsig, I. And Zanetti, M, 2005, Curr. Prot. Pept. Sci. 6:23-34).

The inventors have now found that truncated and mutated versions of the CMAP27 peptide have an excellent antimicrobial activity as well as immunomodulatory properties, typically boosting the immune response, and are preferred as therapeutic compound, because they have a less pronounced effect on blood cells. As is shown in the experimental part, the haemolytic activity of the new antimicrobial peptides of the invention is lower than the haemolytic activity of CMAP27. Further, the peptides of the invention have, at least in several cases, shown a better immunomodulating activity than CMAP27. This latter effect is important, since it potentiates the antimicrobial effect of the peptide.

The peptides of the present invention are truncated forms of the CMAP27 peptide and variants of those, generally indicated herein as CMAP27 derivatives. The peptides are truncated at the C-terminus of the CMAP27 peptide and can have a length of 12-21 amino acids. Apparently thus, the arginine-rich part of the CMAP27 peptide is responsible for the antimicrobial and immunomodulatory effect.

Furthermore, it has appeared that CMAP27 derivatives (with some of the amino acids substituted for by other naturally occurring amino acids), have altered antimicrobial and immunomodulatory activity and, importantly, in which still the low haemolytic activity was maintained. Furthermore, whereas CMAP27 is mainly active on Gram(−) type bacteria, our experiments have shown that several of the CMAP27-derivatives also are effective against Gram(+) type bacteria such as Streptococcus aureus and Bacillus anthracis. It does not need further explanation to realize that such a broadening of the antibiotic spectrum is a clinically very important and relevant finding.

The substitutions that have been tested are all involved with changes in the hydrophilic part of the amphipatic C-terminally truncated (1-15) CMAP27. It has been shown that substitution of one or more of the Phe-residues in this molecule with either leucine or tryptophan results in a molecule with altered activity to CMAP27 or its truncated form. Based on these substitutions it is reasonable that tryptophan-substitutions of the other amino acids in the hydrophobic plain of the peptide, i.e. leucine 6 and isoleucine 9, can similarly improve the antibacterial and immunomodulatory activity of CMAP27 or any of the presented CMAP27 derivatives.

Amino acid substitutions may significantly alter the intricate balance between peptide amphipathicity, net charge, propensity for helix formation, parameters which are linked to peptide stability (formation of self-aggregates in aquaous solutions) and their attachment to and perturbation of biological membranes. Moreover, single or multiple amino acid substitions may render peptide variants less cytotoxic, while maintaining microbicidal and/or immunomodulatory activities. In addition, amino acid substitutions may provide partial protection against proteolytic enzymes.

From the results it also appears that the arginine residue on position 1 of CMAP27 is important for the antimicrobial activity, since all peptides tested where this first residue was removed did not or only hardly show any antimicrobial activity anymore. The situation at the C-terminal end of the truncated peptide seems less restricted, and this thus would allow for further modification of the C-terminal end of the CMAP27-derivative. Modification of one or both termini could include N-terminal acetylation and/or C-terminal amidation, modifications which have demonstrated to protect against exoproteases and in that way to significantly prolong the in vivo half-life time of small peptides (Brinckerhoff, L. H. et al., In. J. Cancer 1999, 83:326). Modification of one or both termini also allows for coupling of the peptide to other moieties, such as other amino acid sequences (thereby possibly creating multimeric proteins), or other biomolecules, which can function as carrier or label. In a specific embodiment the carrier molecule also functions as a targeting molecule, which is able to localise the bacterial infection and can bind to the bacterium, in order to bring the antibiotic compound in the vicinity of the (bacterial) cell to attack.

The term "peptide" as used herein means a sequence of amino acids coupled by a peptide bond, wherein the amino acids are one of the twenty naturally peptide-building amino acids and wherein the amino acids can be in the L-configuration or in the D-configuration, or, for isoleucine and threonine in the D-allo configuration (only inversion at one of the chiral centers). A peptide according to the invention can be linear, i.e. wherein the first and last amino acids of the sequence have a free $NH_2$— or COOH-group respectively or are N-terminally (acetylation) and/or C-terminally (amidation) modified.

The peptides of the invention can be produced synthetically or, where applicable, recombinantly by conventional methods. Specific embodiments of CMAP27-derived antibiotic peptides are disclosed in detail in the experimental part below. Preferably, the peptides or peptide derivatives of the invention are prepared conventionally by known chemical synthesis techniques, such as, for instance, are disclosed by Merrifield (J. Am. Chem. Soc. (1963) 85:2149-2154).

Alternatively, the peptides of the invention may be produced by recombinant DNA techniques by cloning and expressing within a host micro-organism or cell a DNA fragment carrying a nucleic acid sequence encoding one of the above-described peptides. Nucleic acid coding sequences can be prepared synthetically, or may be derived from existing nucleic acid sequences (e.g. the sequence coding for wild-type CMAP27) by site-directed mutagenesis. These nucleic acid sequences may then be cloned in a suitable expression vector and transformed or transfected into a suitable host cell, such as E. coli, Bacillus, Lactobacillus, Streptomyces, mammalian cells (such as CHO, HEK or COS-1 cells), yeasts (e.g. Saccharomyces, Schizophyllum), insect cells or viral expression systems, such as baculovirus systems, or plant cells. A person skilled in the art will have knowledge of the techniques of constructing the nucleic acid sequences and providing means to enable their expression.

Specifically plant cells could be used advantageously for expression of the peptides of the invention, since the peptide in such a case could orally be administered to a human or animal directly, i.e. without any further purification.

Subsequently, the peptide can be isolated from the culture of the host cells. This can be achieved by common protein purification and isolation techniques, which are available in the art. Such techniques may e.g. involve immunoadsorption or chromatography. It is also possible to provide the peptides with a tag (such as a histidine tag) during synthesis, which allows for a rapid binding and purification, after which the tag is enzymatically removed to obtain the active peptide.

Alternatively, the peptides can be produced in cell-free systems, such as the EXPRESSWAY™ cell-free system of INVITROGEN™.

Some more comprehensive summaries of methods which can be applied in the preparation of the peptides are described in: W. F. Anderson, Nature 392 Supp., 30 Apr. 1998, p. 25-30; Pharmaceutical Biotechnology, Ed. D. J. A. Crommelin and R. D. Sindelar, Harwood Academic Publishers, 1997, p. 53-70, 167-180, 123-152, 8-20; Protein Synthesis: Methods and Protocols, Ed. R. Martin, Humana Press, 1998, p. 1-442; Solid-Phase Peptide Synthesis, Ed. G. B. Fields, Academic Press, 1997, p. 1-780; Amino Acid and Peptide Synthesis, Oxford University Press, 1997, p. 1-89.

Novel peptides according to the formula of claim 1 can be readily made by a person skilled in the art.

The CMAP27-derivatives of the invention may be used alone, or in combination in the form of multimers. Suitable combinations of peptides of the invention comprise concatemers of peptides of the invention serially coupled to each other via spacers, for instance in the form of a peptide dimer, a peptide trimer, etc., wherein the individual peptides are subsequently aligned. Single peptide or peptidomimetic chains may be coupled to a biocompatible protein, such as human serum albumin, humanized antibody, liposome, micelle, synthetic polymer, nanoparticle, and phage. Alternatively, multimers of individually combined peptides of the invention may be prepared in the form of dendrimers, or clusters, wherein three or more peptides are linked to one common centre.

Yet other combinations in the form of multimers may be formed by beads on the surface of which the peptides of the invention are exposed. The bead may then function as a carrier for the peptide, and may similarly function as a detectable label. Multimers can, for example, be prepared by biotinylating the N-terminus of peptide chains and subsequent complexation with streptavidin. As streptavidin is able to bind 4 biotin molecules or conjugates with high affinity, very stable tetrameric peptide complexes can be formed by this method. Multimers may be composed of identical or different peptides or peptidomimetics according to the invention. Preferably, however, the multimers of the invention are composed of two or more peptides or peptidomimetics, in which each component constitutes to one asset of the total biocidal activity (targeting, antimicrobial activity, scavenging).

A pharmaceutical composition of the invention comprises a therapeutically effective amount of one or more CMAP27 derivatives of the present invention. Once formulated, the pharmaceutical compositions of the invention can be administered directly to the subject in a method of treating bacterial infection comprising administering to a subject in need thereof a therapeutically effective amount of the composition of the invention.

Direct delivery of the compositions will generally be accomplished by topical application or other forms of administration, either orally, parenterally, subcutaneously, sublingually, intralesionally, intraperitoneally, intravenously or intramuscularly, pulmonarily, or delivered to the interstitial space of a tissue.

The pharmaceutical composition may also comprise a suitable pharmaceutically acceptable carrier or diluent and may be in the form of a capsule, tablet, lozenge, dragee, pill, droplet, suppository, powder, spray, vaccine, ointment, paste, cream, inhalant, patch, aerosol, and the like. As pharmaceutically acceptable carrier, any solvent, diluent or other liquid vehicle, dispersion or suspension aid, surface active agent, isotonic agent, thickening or emulsifying agent, preservative, encapsulating agent, solid binder or lubricant can be used which is most suited for a particular dosage form and which is compatible with the peptide or peptide conjugate.

A pharmaceutical composition may thus contain a pharmaceutically acceptable carrier. The term "pharmaceutically acceptable carrier" also includes a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Salts of peptides or functional equivalents are prepared by known methods, which typically involve the mixing of the peptide with either a pharmaceutically acceptable acid to form an acid addition salt, or with a pharmaceutically acceptable base to form a base addition salt. Whether an acid or a base is pharmaceutically acceptable can be easily decided by a person skilled in the art after taking the specific intended use of the compound into consideration. For instance, not all acids and bases that are acceptable for ex vivo applications can be used for therapeutic compositions. Depending on the intended use, pharmaceutically acceptable acids include organic and inorganic acids such as formic acid, acetic acid, propionic acid, lactic acid, glycolic acid, oxalic acid, pyruvic acid, succinic acid, maleic acid, malonic acid, cinnamic acid, sulfuric acid, hydrochloric acid, hydrobromic acid, nitric acid, perchloric acid, phosphoric acid, and thiocyanic acid, which form ammonium salts with free amino groups of peptides and functional equivalents. Pharmaceutically acceptable bases, which form carboxylate salts with free carboxylic groups of peptides and functional equivalents, include ethylamine, methylamine, dimethylamine, triethylamine, isopropylamine, diisopropylamine, and other mono-, di- and trialkylamines, as well as arylamines. Moreover, also pharmaceutically acceptable solvates are encompassed.

Pharmaceutically acceptable salts can be used herein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

For therapeutic treatment, the peptide or peptide-conjugate may be produced as described above and applied to the subject in need thereof. The peptide or peptide-conjugate may be administered to a subject by any suitable route, preferably in the form of a pharmaceutical composition adapted to such a route and in a dosage that is effective for the intended treatment.

Pharmaceutical compositions of this invention may contain other active agents, such as conventional antibiotics (like e.g. vancomycin, streptomycin, tetracyclin, penicillin) or other antimicrobial compounds, such as anti-fungals, e.g. itraconazole or myconazole. Also compounds that alleviate other infection symptoms, such as fever (e.g. salicylic acid) or skin rash may be added.

Therapeutically effective dosages of the peptide or peptide-conjugate required for treating a bacterial infection in the body of a human or animal subject, can easily be determined by the skilled person, for instance by using animal models.

The term "therapeutically effective amount" as used herein refers to an amount of a therapeutic, viz. a peptide or peptide-conjugate according to the present invention, to reduce or prevent growth and colonization of bacteria, or to exhibit a detectable therapeutic or prophylactic effect. The effect can be detected by, for example, culturing biopsies and assaying for bacterial activity or by any other suitable method of assessing the progress or severity of bacterial infection. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgment of the clinician or experimenter. Specifically, the compositions of the present invention can be used to reduce or prevent bacterial infection and/or accompanying biological or physical manifestations, such as reduction of fever. Methods that permit the clinician to establish initial dosages are known in the art. The dosages determined to be administered must be safe and efficacious.

For purposes of the present invention, an effective dose will be from about 0.01 µg/kg to 50 mg/kg, preferably 0.5 µg/kg to about 10 mg/kg of the peptide or peptide-conjugate in the individual to which it is administered. Dosages for achieving the therapeutic effects of the pharmaceutical composition described herein may easily be determined by the skilled person.

Yet in another alternative embodiment, the peptide or peptide-conjugate or compositions of the invention may be administered from a controlled or sustained release matrix inserted in the body of the subject.

It may also be advantageous to administer a compound of the invention in a transmucosal dosage form. This route of administration is non-invasive and patient-friendly; at the same time it may lead to an improved bioavailability of the compound compared to oral administration, especially if the compound is not stable in the fluids of the digestive system, or if it is too large to be absorbed from the gut effectively. Transmucosal administration is possible, for instance, via nasal, buccal, sublingual, gingival, or vaginal dosage forms. These dosage forms can be prepared by known techniques; they can be formulated to represent nasal drops or sprays, inserts, films, patches, gels, ointments, or tablets. Preferably, the excipients used for a transmucosal dosage form include one or more substances providing for mucoadhesion, thus prolonging the contact time of the dosage form with the site of absorption and thereby potentially increasing the extent of absorption.

In a further embodiment, the compounds are administered via the pulmonary route, using a metered dose inhaler, a nebulizer, an aerosol spray, or a dry powder inhaler. Appropriate formulations can be prepared by known methods and techniques. Transdermal, rectal, or ocular administration may also be feasible in some cases.

It can be advantageous to use advanced drug delivery or targeting methods to deliver a compound of the invention more effectively. For instance, if a non-parenteral route of administration is chosen, an appropriate dosage form may contain a bioavailability enhancing agent, which may be any substance or mixture of substances which increases the availability of the compound. This may be achieved, for instance, by the protection of the compound from degradation, such as by an enzyme inhibitor or an antioxidant. More preferably, the enhancing agent increases the bioavailability of the compound by increasing the permeability of the absorption barrier, which is typically a mucosa. Permeation enhancers can act via various mechanisms; some increase the fluidity of mucosal membranes, while others open or widen the gap junctions between mucosal cells. Still others reduce the viscosity of the mucus covering the mucosal cell layer. Among the preferred bioavailability enhancers are amphiphilic substances such as cholic acid derivatives, phospholipids, ethanol, fatty acids, oleic acid, fatty acid derivatives, EDTA, carbomers, polycarbophil, and chitosan.

Indications for which the CMAP27-derivatives of the invention can be used are bacterial infections by both Gram-positive and Gram-negative bacteria, such as *E. coli, Agrobacterium tumefaciens, Salmonella typhimurum, Erwinia carotovora, E. herbicola, E. chrysanthemi, Klebsiella pneumoniae, Haemophilus influenzae, Francisella tularensis, Bacillus anthracis, Bacillus megaterium, Clostridium botulinum, Vibria cholerae, Bacillus anthracis, Brucella* spp., *Coxiella burnetii, Yersinia pestis, Listeria monocytogenes, Mycobacterium tuberculosis, Pasteurella aeruginosa, Pneumococcus* spp., *Salmonella* spp., *Streptococcus* spp., *Staphylococcus aureus, Staphylococcus pyrogenes, Micrococcus luteus, Moraxella, Neisseria ghonnorhoea, Aerobacter, Borellia*.

Next to therapeutic use for treatment of infections, also in biological warfare, it is also possible to use the antibiotic peptides of the invention in a bactericidal composition that can be used to clean surfaces and/or equipment. Another field of application is in packaging, where peptides can be linked to or embedded in packaging material for packaging of food or other material that is easily degradable by micro-organisms. The CMAP27 derivatives of the invention are specifically usable for packaging, since they are not toxic upon contact or ingestion.

In another embodiment of the invention, the CMAP27 derivatives, but also the full length CMAP27, or its amidated version CMAP1-26-NH2, may be used to boost the immune system. In this respect they can be part of immunologic compositions, especially vaccine compositions, in which they can act as adjuvant. An adjuvant is a substance that enhances the immune response stimulated by an antigen when administered with the antigen. Accordingly, part of the invention are immunologic compositions comprising an antigen and one or more CMAP27 peptides chosen from the group consisting of CMAP27 derivatives as disclosed herein, the full length CMAP27, and its amidated version CMAP1-26-NH$_2$. Similarly also vaccine compositions comprising an antigen and one or more CMAP27 peptides chosen from the group consisting of CMAP27 derivatives as disclosed herein, the full length CMAP27, and its amidated version CMAP1-26-NH$_2$ form part of the present invention, as does the use of the aforementioned compounds as adjuvant.

EXAMPLES

Example 1—Antimicrobial Activity

Isolates of bacteria of e.g. *Vibrio cholera* (BM301), *Staphylococcus aureus* (BM253), *Bacillus* anthracia (BM233) and *Yersinia pestis* (BM360) were seeded on Tryptic Soy Agar (TSA) medium. From each of these cultures one colony was used to be seeded into fluid Brain Heart Infusion (BHI) medium. The bacterial cultures were grown overnight at 35° C. under aerobic conditions. Antibacterial assays were performed in honeycomb 100-well plates (Labsystems Honeycomb 2 plate, with cover 100 pcs, art. No. 9502550) with a final volume of 100 µL BHI per well. Test peptides were diluted in BHI to give a start concentration of 250 µg/ml and serially diluted further. The bacterial culture was 1:10 diluted in HBI and after 2 hours of further culturing diluted to a concentration of about 10⁶ CFU/mL and inoculated into the micro titer plate wells(10 µL). Plates were incubated while gently shaking at 37° C. for 16 h and during this time the growth of the bacteria was measured at 600 nm using a BioScreen C MBR (purchased from Oy Growth Curves Ab Ltd, Helsinki, Finland). After 16 hours, the exact cell density was calculated by plating dilution series (100 µL) on TSA plates (in duplicate). The percentage growth was calculated by the ratio of the growth rate of the control bacteria and the growth rate of the peptide-treated bacteria.

The amino acid sequence of the tested peptides and the score on their antimicrobial activity are presented in Table 1.

Example 2—Haemolytic Activity

Erythrocytes from healthy human individuals and chickens were collected by centrifugation at 75×g for 15 min. Cells were washed three times in PBS, supplemented with 287 mM glucose as osmoprotectant. The cell suspension was normalized to a haemoglobin value of 2 mmol/l in PBS or isotonic glucose phosphate buffer. In a 96-well V bottom microtiter plate purchased from Greiner-Bio-One GmbH (Frickenhausen, Germany), 100 µl of this suspension was added in triplicate to 100 µl of dilution series of peptide in the same buffer, starting with a concentration of 100 µM. After 1 h of incubation at 37° C., the microtiter plates were centrifuged at 550×g for 5 min, and the absorbance in the supernatant was measured at 450 nm. Complete haemolysis was calculated as follows: [(A450 of the peptide treated sample-A450 of buffer treated sample)/((A450 of Tween-20 treated sample-A450 of buffer treated sample)]×100%. The results are given in Table 1 and 2 according to the following scheme:
Score haemolysis
>75% dead cells ++
>50% dead cells +
>25% dead cells +/−
<25% dead cells−
<5% dead cells −−

Example 3—Immunomodulating Activity: LPS Neutralisation

Next to screening on antimicrobial and haemolytic activity, the CMAP27 derivatives of the invention have also been assayed for their immunomodulating activities.

One of the tested immunomodulating properties is the neutralising capacity directed against an abundant and deleterious immune response against endotoxins, such as LPS (lipopolysaccharides). An assay was performed which allowed to determine the LPS neutralizing capacity of CMAP27 and CMAP27 derivatives in the presence of primary human cells (PBMCs: Peripheral Blood Mononuclear Cells), a human cell line (THP-1: Human acute monocytic leukemia cell line) and a chicken cell line (HD11: Chicken macrophage cell line).

PBMCs and THP-1 cells were seeded in 96 well plates (1×10⁶ cells/well). HD11 cells were seeded in 96 well plates at a concentration 3×105 cells/well. Subsequently they were stimulated with LPS in the presence or absence of the testcompound during 5 or 24 hours. After stimulation of PBMCs and THP-1 cells, the supernatant was assayed for the amount of pro-inflammatory cytokines (TNF, IL-6), IL-8 and anti-inflammatory cytokine IL-10 with ELISA. After stimulation of HD11 cells, cells were lysed, after which transcribed RNA was used to determine transcription levels of the inflammatory cytokine IL-1β, IL-8 and chemokines MCP-3 (Monocyte Chemotactic Protein-3) and RANTES by Real-Time PCR. In Table 1 and 2 the data from these experiments are summarized, in which the inhibition of the LPS evoked response is given compared to the response in control cells (100%) according to the following scheme:
>95% inhibition ++
>75% inhibition +
>25% inhibition +/−
<25% inhibition −

Also a migration assay was performed, in which 96-well plates of the CHEMOTX® System (Neuro Probe, Inc.) were used. The peptide is applied to the bottom component of the plates and this was covered with a filter. 50.000 calcein AM labeled THP-1 cells per well were applied to the filter. After incubation for 2 hours the amount of cells that have migrated through the filter could be determined via fluorescence measurement. The results are given in Table 1 according to the following scheme:
>6000 cells migrated ++
>2000 cells migrated
>1000 cells migrated +/−
<1000 cells migrated Example 4—Immunomodulating Activity: Peptide-Induced Cytokine Production In addition to screening of the neutralizing capacity on LPS-induced cytokine production, CMAP27 derivatives have also been assayed for their direct peptide-induced effects on immune cells.

For this purpose, human PBMCs were seeded in 96 well plates (1×106 cells/well) and HD11 cells were seeded in 96 well plates at a concentration 3×10⁵ cells/well. Subsequently they were stimulated with cell culture medium in the presence or absence of CMAP27 derivatives during 4 (HD11), 5 (PBMCs) or 24 hours. After stimulation of PBMCs, the supernatant was assayed for the amount of chemokine MCP-1 (Monocyte Chemotactic Protein-1) with ELISA. After stimulation of HD11 cells, cells were lysed, after which transcribed RNA was used to determine transcription levels of IL-1β, IL-8, MCP-3 and RANTES by Real-Time PCR.

In Table 1 and 2 the data from these experiments are summarized, in which the peptide-induced response is given compared to the response in control cells (100%) according to the following scheme:
Peptide-Induced MCP-1 Production as Determined by ELISA:
>480% MCP-1 production (>95% of max.) ++
>400% MCP-1 production (>75% of max.) +
>200% MCP-1 production (>25% of max.) +/−
<200% MCP-1 production (<25% of max.) −
Peptide-Induced Cytokine Production as Determined by Real-Time PCR:
>8-fold increase in gene expression levels ++
>4-fold increase in gene expression levels +
>2-fold increase in gene expression levels +/−
<2-fold increase in gene expression levels −

TABLE 1

| name | Sequence | Toxicity Haemolysis (hRBCs) | Antibacterial activity Gram (−) V. cholera | Antibacterial activity Gram (−) Y. pestis | Antibacterial activity Gram (+) S. aureus | Antibacterial activity Gram (+) B. anthracis | Immune-modulation LPS neutralisation hPBMCs TNFα |
|---|---|---|---|---|---|---|---|
| CMAP27 | RFGRFLRKIRRFRPKVTITIQGSARFG (SEQ ID NO: 1) | − | +/− | ++ | − | − | ++ |
| CMAP26-NH2 | RFGRFLRKIRRFRPKVTITIQGSARF-NH2 (SEQ ID NO: 8) |  |  |  |  |  | ++ |
| CMAP26 | RFGRFLRKIRRFRPKVTITIQGSARF (SEQ ID NO: 9) | ++ | ++ | ++ | − | − | ++ |
| CMAP26 (P14→G) | RFGRFLRKIRRFRGKVTITIQGSARF (SEQ ID NO: 10) | − | +/− | ++ | − | − | ++ |
| CMAP26 (P14→L) | RFGRFLRKIRRFRLKVTITIQGSARF (SEQ ID NO: 11) | − | − | + | − | − | + |
| CMAP1-21 | RFGRFLRKIRRFRPKVTITIQ (SEQ ID NO: 12) |  |  |  |  |  | + |
| CMAP(1-15) | RFGRFLRKIRRFRPK (SEQ ID NO: 7) | −− | +/− | +/− | − | − | + |
| CMAP(1-15) (F2→L) | RLGRFLRKIRRFRPK (SEQ ID NO: 13) | − | − | ++ | +/− | ++ | +/− |
| CMAP(1-15) (F5→L) | RFGRLLRKIRRFRPK (SEQ ID NO: 14) | − |  |  |  |  | − |
| CMAP(1-15) (F12→L) | RFGRFLRKIRRLRPK (SEQ ID NO: 15) | − | +/− | ++ | +/− | +/− | +/− |
| CMAP(1-15) (3xF→L) | RLGRLLRKIRRLRPK (SEQ ID NO: 16) | − | +/− | ++ | − | + | + |
| CMAP(1-15) (F2→W) | RWGRFLRKIRRFRPK (SEQ ID NO: 17) | −− | +/ | + | + | ++ | + |
| CMAP(1-15) (F5→W) | RFGRWLRKIRRFRPK (SEQ ID NO: 18) | −− | +/− | ++ | ++ | ++ | + |
| CMAP(1-15) (F12→W) | RFGRFLRKIRRWRPK (SEQ ID NO: 19) | −− | +/− | − | + | ++ | + |
| CMAP(1-15) (3xF→W) | RWGRWLRKIRRWRPK (SEQ ID NO: 20) | − | +/− | − | + | ++ | ++ |
| CMAP(1-13) | RFGRFLRKIRRFR (SEQ ID NO: 21) | −− | +/− | +/− | − | − | − |
| CMAP(1-12) | RFGRFLRKIRRF (SEQ ID NO: 22) | −− | − | +/− | − | − | − |
| CMAP(1-11) | RFGRFLRKIRR (SEQ ID NO: 23) | +/− | − | + | − | − | − |
| CMAP(1-10) | RFGRFLRKIR (SEQ ID NO: 24) | −− | − | + | − | − | − |
| CMAP(2-15) | FGRFLRKIRRFRPK (SEQ ID NO: 25) | −− | − | − | − | − | − |
| CMAP(3-15) | GRFLRKIRRFRPK (SEQ ID NO: 26) | −− | − | − | − | − | − |
| CMAP(4-15) | RFLRKIRRFRPK (SEQ ID NO: 27) | +/− | − | − | − | − | − |
| CMAP(5-15) | FLRKIRRFRPK (SEQ ID NO: 28) | − | − | − | − | − | − |

| name | Immune-modulation LPS neutralisation hPBMCs IL-6 | Immune-modulation LPS neutralisation hPBMCs IL-8 | Immune-modulation LPS neutralisation hPBMCs IL-10 | Immune-modulation LPS neutralisation THP-1 TNFα | Peptide-induced hPBMCs MCP-1 | Migration THP-1 |
|---|---|---|---|---|---|---|
| CMAP27 | + | +/− | + | + | ++ | +/− |
| CMAP26-NH2 | + | − | + |  | ++ |  |
| CMAP26 | ++ | +/− | ++ | + | + | − |
| CMAP26 (P14→G) | ++ | + | ++ | + | ++ | − |
| CMAP26 (P14→L) | − | +/− | + | ++ | − | − |
| CMAP1-21 | − | − | +/− |  | ++ |  |
| CMAP(1-15) | +/− | − | + | + |  | − |
| CMAP(1-15) (F2→L) | − |  |  | + |  | − |
| CMAP(1-15) (F5→L) | − |  |  | +/− |  | − |
| CMAP(1-15) (F12→L) | − |  |  | + |  | − |
| CMAP(1-15) (3xF→L) | − |  |  | + |  | − |
| CMAP(1-15) (F2→W) | +/− |  |  | + |  | + |
| CMAP(1-15) (F5→W) | +/− |  |  | + |  | + |
| CMAP(1-15) (F12→W) | + |  |  | + |  | + |
| CMAP(1-15) (3xF→W) | ++ |  |  | + |  | ++ |

TABLE 1-continued

| | | | |
|---|---|---|---|
| CMAP(1-13) | – | +/– | – |
| CMAP(1-12) | – | + | – |
| CMAP(1-11) | – | +/– | – |
| CMAP(1-10) | – | +/– | – |
| CMAP(2-15) | – | – | – |
| CMAP(3-15) | – | – | – |
| CMAP(4-15) | – | – | – |
| CMAP(5-15) | – | – | – |

TABLE 2

| name | Sequence | Toxicity Haemolysis (cRBCs) | Immune-modulation LPS neutralisation HD11 | | | | Peptide-induced HD11 | | | |
|---|---|---|---|---|---|---|---|---|---|---|
| | | | IL-1β | IL-8 | MCP-3 | RANTES | IL-1β | IL-8 | MCP-3 | RANTES |
| | | | 4 h stimulation | | | | | | | |
| CMAP26-$_{NH2}$ | RFGRFLRKIRRFRPKVTITIQGSARF-$_{NH2}$ (SEQ ID NO: 8) | +/– | + | – | – | +/– | ++ | ++ | + | ++ |
| CMAP1-21 | RFGRFLRKIRRFRPKVTITIQ (SEQ ID NO: 12) | – | – | – | – | +/– | +/– | + | + | ++ |
| CMAP(1-15) | RFGRFLRKIRRFRPK (SEQ ID NO: 7) | – | – | – | – | – | – | +/– | +/– | +/– |
| | | | 24 h stimulation | | | | | | | |
| CMAP26-$_{NH2}$ | RFGRFLRKIRRFRPKVTITIQGSARF-$_{NH2}$ (SEQ ID NO: 8) | | | | | | – | – | – | – |
| CMAP1-21 | RFGRFLRKIRRFRPKVTITIQ (SEQ ID NO: 12) | | | | | | +/– | – | + | + |
| CMAP(1-15) | RFGRFLRKIRRFRPK (SEQ ID NO: 7) | | | | | | – | – | – | – |

The invention claimed is:

1. A method of modulating an immune response in an animal in need thereof, the method comprising administering CMAP1-21 (SEQ ID NO: 11) or a C-terminal amide thereof, to the animal in need thereof, wherein said modulating stimulates the immune response.

2. The method according to claim 1, wherein said immune response comprises neutralization of lipopolysaccharide (LPS) induced cytokine production.

3. The method according to claim 2, wherein said cytokine comprises tumor necrosis factor alpha (TNF alpha).

4. The method according to claim 2, wherein said cytokine comprises interleukin-10 (IL-10).

5. The method according to claim 1, wherein the immune response comprises peripheral blood mononuclear cell (PBMC) migration.

6. The method according to claim 1, wherein the immune response comprises a release of a chemokine selected from the group consisting of monocyte chemoattractant protein-1 (MCP-1), monocyte chemoattractant protein-3 (MCP-3), and Regulated upon Activation, Normal Cell Expressed and Presumably Secreted (RANTES).

7. The method according to claim 6, wherein the chemokine is MCP 1.

8. The method according to claim 1, wherein said immune response comprises an increase in production of RANTES, MCP-1, MCP-3, interleukin-8 (IL-8), or interleukin-1 beta (IL-1 beta).

9. The method according to claim 1, wherein said immune response comprises at least one of:
   a) neutralization of LPS-induced cytokine production;
   b) PBMC migration;
   c) chemokine release; or
   d) an increase in production of at least one member of the group consisting of RANTES, MCP-1, MCP-3, IL-8, and IL-1 beta.

10. The method according to claim 9, wherein said immune response comprises neutralization of LPS-induced cytokine production, and wherein said cytokine is selected from the group consisting of TNF alpha and IL-10.

* * * * *